(12) United States Patent
Fisher et al.

(10) Patent No.: US 8,043,334 B2
(45) Date of Patent: Oct. 25, 2011

(54) ARTICULATING FACET FUSION SCREW

(75) Inventors: Michael Alan Fisher, Middleborough, MA (US); Christopher Mickiewicz, Bridgewater, MA (US)

(73) Assignee: DePuy Spine, Inc., Raynham, MA (US)

( * ) Notice: Subject to any disclaimer, the term of this patent is extended or adjusted under 35 U.S.C. 154(b) by 298 days.

(21) Appl. No.: 11/734,877

(22) Filed: Apr. 13, 2007

(65) Prior Publication Data
US 2008/0255618 A1   Oct. 16, 2008

(51) Int. Cl.
*A61B 17/70* (2006.01)
(52) U.S. Cl. ......... 606/247; 606/300; 606/301; 606/310
(58) Field of Classification Search ............... 606/247, 606/300–321, 246, 264–279; 623/17.11–17.16
See application file for complete search history.

(56) References Cited

U.S. PATENT DOCUMENTS

| | | |
|---|---|---|
| 3,934,444 A | 1/1976 | Simons |
| 4,011,602 A | 3/1977 | Rybicki et al. |
| 4,263,904 A | 4/1981 | Judet et al. |
| 4,590,928 A | 5/1986 | Hunt et al. |
| 4,858,603 A | 8/1989 | Clemow et al. |
| 4,878,794 A | 11/1989 | Potucek |
| 4,898,186 A | 2/1990 | Ikada et al. |
| 4,927,421 A | 5/1990 | Goble et al. |
| 4,961,740 A | 10/1990 | Ray et al. |
| 4,988,351 A | 1/1991 | Paulos et al. |
| 5,059,193 A | 10/1991 | Kuslich |
| 5,100,405 A * | 3/1992 | McLaren ............ 606/304 |
| 5,129,904 A | 7/1992 | Illi |
| 5,152,303 A | 10/1992 | Allen |
| 5,156,616 A | 10/1992 | Meadows et al. |
| 5,169,400 A | 12/1992 | Muhling et al. |
| 5,180,388 A | 1/1993 | DiCarlo |
| 5,275,601 A | 1/1994 | Gogolewski et al. |
| 5,314,427 A | 5/1994 | Goble et al. |
| 5,364,400 A | 11/1994 | Rego, Jr. et al. |
| 5,403,136 A | 4/1995 | Mathys et al. |
| 5,409,486 A | 4/1995 | Reese |
| 5,443,509 A | 8/1995 | Boucher et al. |

(Continued)

FOREIGN PATENT DOCUMENTS

EP   0502698   9/1992

(Continued)

OTHER PUBLICATIONS

International Search Report and Report Opinion dated Sep. 16, 2008 for PCT/US08/59889.

(Continued)

*Primary Examiner* — Eduardo C Robert
*Assistant Examiner* — Christina Negrelli
(74) *Attorney, Agent, or Firm* — Nutter McClennen & Fish LLP

(57) ABSTRACT

A spinal implant is provided having an elongate member with a longitudinal axis and threads extending over at least a portion of the outer surface thereof. The implant includes a stabilization feature associated with the elongate member that is selectively configurable between a delivery configuration and a deployed configuration in which the stabilization feature is oriented at an angle with respect to the longitudinal axis of the elongate member. Also, at least a portion of the implant can include a fusion-promoting bioactive material. In another aspect, the invention includes methods for providing stabilization within a facet joint by delivery of an articulating intra-facet screw.

20 Claims, 15 Drawing Sheets

U.S. PATENT DOCUMENTS

| | | |
|---|---|---|
| 5,456,685 A | 10/1995 | Huebner |
| 5,470,334 A | 11/1995 | Ross et al. |
| D368,777 S | 4/1996 | Goble et al. |
| 5,527,312 A | 6/1996 | Ray |
| 5,545,163 A | 8/1996 | Miller et al. |
| 5,558,674 A | 9/1996 | Heggeness et al. |
| D374,286 S | 10/1996 | Goble et al. |
| D374,287 S | 10/1996 | Goble et al. |
| D374,482 S | 10/1996 | Goble et al. |
| 5,562,672 A | 10/1996 | Huebner et al. |
| 5,571,104 A | 11/1996 | Li |
| 5,571,139 A | 11/1996 | Jenkins, Jr. |
| 5,613,968 A | 3/1997 | Lin |
| 5,645,547 A | 7/1997 | Coleman |
| 5,697,929 A | 12/1997 | Mellinger |
| 5,743,912 A | 4/1998 | Lahille et al. |
| 5,743,914 A | 4/1998 | Skiba |
| 5,840,078 A | 11/1998 | Yerys |
| 5,871,486 A | 2/1999 | Huebner et al. |
| 5,885,300 A | 3/1999 | Tokuhashi et al. |
| 5,888,228 A | 3/1999 | Knothe et al. |
| 5,925,047 A | 7/1999 | Errico et al. |
| 5,947,969 A | 9/1999 | Errico et al. |
| 5,951,560 A | 9/1999 | Simon et al. |
| 5,964,761 A | 10/1999 | Kambin |
| 5,968,047 A | 10/1999 | Reed |
| 5,989,255 A | 11/1999 | Pepper et al. |
| 6,030,162 A | 2/2000 | Huebner |
| 6,045,554 A | 4/2000 | Grooms et al. |
| 6,048,343 A | 4/2000 | Mathis et al. |
| 6,080,157 A | 6/2000 | Cathro et al. |
| 6,096,060 A | 8/2000 | Fitts et al. |
| 6,099,529 A | 8/2000 | Gertzman et al. |
| 6,126,663 A | 10/2000 | Hair |
| 6,162,225 A | 12/2000 | Gertzman et al. |
| 6,214,007 B1 | 4/2001 | Anderson |
| 6,214,012 B1 | 4/2001 | Karpman et al. |
| 6,277,149 B1 | 8/2001 | Boyle et al. |
| 6,283,973 B1 | 9/2001 | Hubbard et al. |
| 6,383,187 B2 | 5/2002 | Tormala et al. |
| 6,402,757 B1 | 6/2002 | Moore, III et al. |
| 6,461,373 B2 | 10/2002 | Wyman et al. |
| 6,464,706 B1 | 10/2002 | Winters |
| 6,485,518 B1 | 11/2002 | Cornwall et al. |
| 6,488,683 B2 | 12/2002 | Lieberman |
| 6,506,192 B1 | 1/2003 | Gertzman et al. |
| 6,527,773 B1 | 3/2003 | Lin et al. |
| 6,540,747 B1 | 4/2003 | Marino |
| 6,565,572 B2 | 5/2003 | Chappius |
| 6,569,186 B1 | 5/2003 | Winters et al. |
| 6,585,518 B1 | 7/2003 | Jenkins et al. |
| 6,589,245 B1 | 7/2003 | Weiler et al. |
| 6,629,977 B1 | 10/2003 | Wolf |
| 6,641,583 B2 | 11/2003 | Shluzas et al. |
| 6,648,893 B2* | 11/2003 | Dudasik .................. 606/327 |
| 6,666,868 B2 | 12/2003 | Fallin |
| 6,685,706 B2 | 2/2004 | Padget et al. |
| 6,723,095 B2 | 4/2004 | Hammerslag |
| 6,808,526 B1 | 10/2004 | Magerl et al. |
| 6,811,567 B2 | 11/2004 | Reiley |
| 6,921,402 B2 | 7/2005 | Contiliano et al. |
| 6,923,814 B1 | 8/2005 | Hildebrand et al. |
| 6,945,975 B2 | 9/2005 | Dalton |
| 6,966,930 B2 | 11/2005 | Arnin et al. |
| 6,979,333 B2 | 12/2005 | Hammerslag |
| 6,981,974 B2 | 1/2006 | Berger |
| 7,056,341 B2 | 6/2006 | Crozet |
| 7,090,675 B2 | 8/2006 | Songer |
| 7,101,398 B2 | 9/2006 | Dooris et al. |
| 7,410,789 B2 | 8/2008 | Schlosser et al. |
| 7,491,221 B2 | 2/2009 | David |
| 7,708,761 B2 | 5/2010 | Peterson |
| 7,799,057 B2* | 9/2010 | Hudgins et al. ............ 606/247 |
| 7,909,826 B2 | 3/2011 | Serhan et al. |
| 2001/0029375 A1 | 10/2001 | Betz et al. |
| 2002/0042615 A1 | 4/2002 | Graf et al. |
| 2002/0151895 A1 | 10/2002 | Soboleski et al. |
| 2002/0177898 A1 | 11/2002 | Crozet |
| 2002/0183747 A1 | 12/2002 | Jao et al. |
| 2003/0032960 A1 | 2/2003 | Dudasik |
| 2003/0040746 A1 | 2/2003 | Mitchell et al. |
| 2003/0125740 A1 | 7/2003 | Khanna |
| 2003/0153921 A1 | 8/2003 | Stewart et al. |
| 2004/0006342 A1 | 1/2004 | Altarac et al. |
| 2004/0082956 A1 | 4/2004 | Baldwin et al. |
| 2004/0087948 A1 | 5/2004 | Suddaby |
| 2004/0111093 A1 | 6/2004 | Chappuis |
| 2004/0127906 A1 | 7/2004 | Culbert et al. |
| 2004/0127989 A1 | 7/2004 | Dooris et al. |
| 2004/0143267 A1 | 7/2004 | Fallin |
| 2004/0143268 A1 | 7/2004 | Falahee |
| 2004/0167520 A1 | 8/2004 | Zucherman et al. |
| 2004/0186475 A1 | 9/2004 | Falahee |
| 2004/0225292 A1 | 11/2004 | Sasso et al. |
| 2004/0225360 A1 | 11/2004 | Malone |
| 2004/0230192 A1 | 11/2004 | Graf |
| 2004/0249376 A1 | 12/2004 | Hammerslag |
| 2004/0254575 A1 | 12/2004 | Obenchain et al. |
| 2004/0260296 A1 | 12/2004 | Kaiser et al. |
| 2004/0260298 A1 | 12/2004 | Kaiser et al. |
| 2005/0015060 A1 | 1/2005 | Sweeney |
| 2005/0038434 A1 | 2/2005 | Mathews |
| 2005/0113929 A1* | 5/2005 | Cragg et al. ............... 623/17.16 |
| 2005/0119657 A1 | 6/2005 | Goldsmith |
| 2005/0124993 A1 | 6/2005 | Chappuis |
| 2005/0149030 A1 | 7/2005 | Serhan et al. |
| 2005/0165399 A1 | 7/2005 | Michelson |
| 2005/0177240 A1 | 8/2005 | Blain |
| 2005/0192572 A1 | 9/2005 | Abdelgany et al. |
| 2005/0197660 A1 | 9/2005 | Haid et al. |
| 2005/0197700 A1 | 9/2005 | Boehm et al. |
| 2005/0216016 A1 | 9/2005 | Contiliano et al. |
| 2005/0222681 A1 | 10/2005 | Richley et al. |
| 2005/0228384 A1 | 10/2005 | Zucherman et al. |
| 2005/0234551 A1 | 10/2005 | Fallin et al. |
| 2005/0234552 A1 | 10/2005 | Reiley |
| 2005/0240188 A1* | 10/2005 | Chow et al. .................... 606/72 |
| 2005/0251256 A1 | 11/2005 | Reiley |
| 2005/0261770 A1 | 11/2005 | Kuiper et al. |
| 2005/0267480 A1 | 12/2005 | Suddaby |
| 2005/0273110 A1 | 12/2005 | Boehm et al. |
| 2006/0004358 A1 | 1/2006 | Serhan et al. |
| 2006/0004367 A1 | 1/2006 | Alamin et al. |
| 2006/0004448 A1 | 1/2006 | Casey |
| 2006/0004449 A1 | 1/2006 | Goble et al. |
| 2006/0004451 A1 | 1/2006 | Goble et al. |
| 2006/0009847 A1 | 1/2006 | Reiley |
| 2006/0009848 A1 | 1/2006 | Reiley |
| 2006/0015105 A1* | 1/2006 | Warren et al. .................... 606/72 |
| 2006/0030948 A1 | 2/2006 | Manrique et al. |
| 2006/0036243 A1 | 2/2006 | Sasso et al. |
| 2006/0036323 A1 | 2/2006 | Carl et al. |
| 2006/0041311 A1 | 2/2006 | McLeer |
| 2006/0052785 A1 | 3/2006 | Augostino et al. |
| 2006/0064099 A1 | 3/2006 | Pavlov et al. |
| 2006/0085068 A1 | 4/2006 | Barry |
| 2006/0089646 A1 | 4/2006 | Bonutti |
| 2006/0095036 A1 | 5/2006 | Hammerslag |
| 2006/0095040 A1 | 5/2006 | Schlienger et al. |
| 2006/0106381 A1 | 5/2006 | Ferree et al. |
| 2006/0111179 A1 | 5/2006 | Inamura |
| 2006/0111779 A1 | 5/2006 | Petersen |
| 2006/0111782 A1 | 5/2006 | Petersen |
| 2006/0122609 A1 | 6/2006 | Mirkovic et al. |
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0178743 A1 | 8/2006 | Carter |
| 2006/0190081 A1 | 8/2006 | Kraus et al. |
| 2006/0200137 A1 | 9/2006 | Soboleski et al. |
| 2006/0217714 A1 | 9/2006 | Serhan et al. |
| 2006/0235388 A1 | 10/2006 | Justis et al. |
| 2006/0235391 A1 | 10/2006 | Sutterlin |
| 2006/0241597 A1 | 10/2006 | Mitchell et al. |

| | | |
|---|---|---|
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1* | 11/2006 | Yerby et al. .............. 606/90 |
| 2006/0264953 A1 | 11/2006 | Falahee |
| 2006/0271054 A1* | 11/2006 | Sucec et al. .............. 606/73 |
| 2006/0276790 A1 | 12/2006 | Dawson et al. |
| 2006/0276801 A1 | 12/2006 | Yerby et al. |
| 2006/0293658 A1 | 12/2006 | Sharim |
| 2007/0016191 A1 | 1/2007 | Culbert et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0055236 A1 | 3/2007 | Hudgins et al. |
| 2007/0055373 A1 | 3/2007 | Hudgins et al. |
| 2007/0073290 A1 | 3/2007 | Boehm |
| 2007/0118132 A1 | 5/2007 | Culbert et al. |
| 2007/0135814 A1 | 6/2007 | Farris |
| 2007/0233093 A1 | 10/2007 | Falahee |
| 2007/0250166 A1 | 10/2007 | McKay |
| 2008/0103512 A1 | 5/2008 | Gately |
| 2008/0177334 A1* | 7/2008 | Stinnette .............. 606/304 |
| 2008/0234758 A1 | 9/2008 | Fisher et al. |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0275507 A1 | 11/2008 | Triplett et al. |
| 2008/0306537 A1 | 12/2008 | Culbert |
| 2008/0306555 A1 | 12/2008 | Patterson et al. |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012566 A1 | 1/2009 | Fauth |
| 2009/0036926 A1 | 2/2009 | Hestad |
| 2009/0036986 A1 | 2/2009 | Lancial et al. |
| 2009/0099602 A1 | 4/2009 | Aflatoon |
| 2009/0105716 A1 | 4/2009 | Barrus |
| 2009/0125066 A1 | 5/2009 | Kraus et al. |
| 2009/0138053 A1 | 5/2009 | Assell et al. |
| 2009/0192551 A1 | 7/2009 | Cianfrani et al. |
| 2009/0312763 A1 | 12/2009 | McCormack et al. |

FOREIGN PATENT DOCUMENTS

| | | | |
|---|---|---|---|
| EP | 0856293 A1 | 8/1998 |
| EP | 1210914 A1 | 6/2002 |
| EP | 1248568 A2 | 10/2002 |
| EP | 1452146 A1 | 9/2004 |
| EP | 1585449 A1 | 10/2005 |
| EP | 1813216 A1 | 8/2007 |
| WO | WO-0041636 A1 | 7/2000 |
| WO | 0062684 A1 | 10/2000 |
| WO | 0141681 A1 | 6/2001 |
| WO | WO-0141681 A1 | 6/2001 |
| WO | 0234120 A2 | 5/2002 |
| WO | 03007829 A1 | 1/2003 |
| WO | 2004043278 A1 | 5/2004 |
| WO | 2004100808 A1 | 11/2004 |
| WO | 2004110288 A2 | 12/2004 |
| WO | 2005004733 A1 | 1/2005 |
| WO | 2005042036 A2 | 5/2005 |
| WO | 2005060845 A1 | 7/2005 |
| WO | 2005076974 A2 | 8/2005 |
| WO | 2005097005 A1 | 10/2005 |
| WO | 2006007739 A1 | 1/2006 |
| WO | 2006009855 A2 | 1/2006 |
| WO | WO-2006002684 A1 | 1/2006 |
| WO | 2006047707 A2 | 5/2006 |
| WO | 2006057943 A2 | 6/2006 |
| WO | 2006065774 A1 | 6/2006 |
| WO | 2006086241 A2 | 8/2006 |
| WO | 2006096803 A2 | 9/2006 |
| WO | 2006116119 A2 | 11/2006 |
| WO | 2007019710 A1 | 2/2007 |
| WO | 2007041698 A1 | 4/2007 |
| WO | 2007047711 A2 | 4/2007 |
| WO | 2007063399 A1 | 6/2007 |
| WO | 2007075454 A1 | 7/2007 |
| WO | 2007120903 A2 | 10/2007 |
| WO | 2007127610 A1 | 11/2007 |
| WO | 2008124196 A2 | 10/2008 |
| WO | WO-2008153732 A1 | 12/2008 |
| WO | 2009018220 A1 | 2/2009 |
| WO | 2009067486 A2 | 5/2009 |
| WO | WO-2009138053 A1 | 11/2009 |

OTHER PUBLICATIONS

International Search Report and Written Opinion dated Jul. 25, 2008 for PCT/US08/50194.

International Search Report and Written Opinion dated Sep. 24, 2008 for PCT/US08/59866.

Frank M. Phillips, M.D., "Effect of Supplemental Translaminar Facet Screw Fixation on the Stability of Stand-Alone Anterior Lumbar Interbody Fusion Cages Under Physiologic Compressive Preloads", Spine vol. 29, No. 16, pp. 1731-1736, , Lippincott Williams & Wilkins, Inc © 2004, Augus.

Youssef Masharawi, PhD, et al., "Facet Orientation in the Thoracolumbar Spine", Spine vol. 29, No. 16, pp. 1755-1763, © 2004, Lippincott Williams & Wilkins, Inc.

Brian P. Beaubien, BME, et al., "Posterior Augmentation of an Anterior Lumbar Interbody Fusion", Spine vol. 29, No. 19, pp. E406-E412, © 2004, Lippincott Williams & Wilkins, Inc.

Frank Kandziora, M.D., et al., "Biomechanical Testing of the Lumbar Facet Interference Screw", Spine vol. 30, No. 2, pp. E34-E39, © 2005, Lippincott Williams & Wilkins, Inc.

Neil Duggal, M.D., et al., "Unilateral Cervical Facet Dislocation: Biomechanics of Fixation", Spine vol. 30, No. 7, pp. E164-E168, © 2005, Lippincott Williams & Wilkins, Inc.

Youssef masharawi, PhD, BPT, et al., "Facet Tropism and Interfacet Shape in the Thoracolumbar Vertebrae", Spine vol. 30, No. 11, pp. E281-E292, © 2005, Lippincott Williams & Wilkins, Inc., Aug. 15, 2004.

Brian P. Beaubien, BME, et al., "In Vitro, Biomechanical Comparison of an Anterior Lumbar Interdody Fusion with an Anteriorly Placed, Low-Profile Lumbar Plate and Posteriorly Placed Pedicle Screws or Translaminar Screws", Spine vol. 30, No. 16, pp. 1846-1851, © 2005, Lippincott Williams & Wilkins, Inc.

David W. Polly, Jr., M.D., et al. "Surgical Treatment for the Painful Motion Segment", Spine vol. 30, No. 16S, pp. S44-S51, © 2005, Lippincott Williams & Wilkins, Inc.

Douglas Burton, M.D., et al., "Biomechanical Analysis of Posterior Fixation Techniques in a 360° Arthrodesis Model", Spine vol. 30, No. 24, pp. 2765-2771, © 2005, Lippincott Williams & Wilkins, Inc.

Langston T. Holly, M.D., et al., "Percutaneous Placement of Posterior Cervical Screws Using Three-Dimensional Fluoroscopy", Spine vol. 31, No. 5, pp. 536-540, © 2006, Lippincott Williams & Wilkins, Inc.

Frank M. Phillips, M.D., et al., "Radiographic Criteria for Placement of Translaminar Facet Screws", The Spine Journal 4 (2004) 465-467.

Andrew V. Slucky, M.D., et al., "Less Invasive Posterior Fixation Method Following Transforaminal Lumbar Interbody Fusion: a Biomechanical Analysis", The Spine Journal 6 (2006) 78-85.

U.S. Appl. No. 12/834,397 for "Pedicular Facet Fusion Screw With Plate" filed Jul. 12, 2010.

U.S. Appl. No. 12/834,417 for "Pedicular Facet Fusion Screw With Plate" filed Jul. 12, 2010.

Brain W. Su, MD, et al. "An Anatomic and Radiographic Study of Lumbar Facets Relevant to Percutaneous Transfacet Fixation", Spine vol. 34, No. 11, pp. E384-E390, 2009, Lippincott Williams & Wilkins.

Ch. D. Ray, "Transfacet Decompression with Dowel Fixation: a New Technique for Lumbar Lateral Spinal Stenosis", Acta Neurochirurgica, Suppl. 43, 48-54 (1988) © by Springer-Verlag 1988.

Th.-M. Markwalder, et al, "Translaminar Screw Fixation in Lumbar Spine Pathology", Acta Neurochir (Wien) (1989) 99: 58-60.

Matthijs R. Krijnen, M.D., et al, "Does Bioresorbable Cage Material Influence Segment Stability in Spinal Interbody Fusion?" Clinical Orthopaedics and Related Research, No. 448, pp. 33-38 © 206 Lippincott Williams & Wilkins.

D.A. McQueen, M.D. et al., "Knee Arthrodesis with the Wichita Fusion Nail", Clinical Orthopaedics and Related Research, No. 446, pp. 132-139, © 2006 Lippincott Williams & Wilkins.

D.Grob et al., Translaminar screw fixation in the lumbar spine: technique, indications, results, Eur Spine J (1998) vol. 7:178-186, © Springer-Verlag 1998.

Hans Trouillier, et al., "A Prospective Morphological Study of Facet Joint Integrity Following Intervertebral Disc Replacement with the CHARITE™ Artificial Disc", Eur Spine J. (2006) vol. 15: 174-182 DOI 10.1007/s00586-005-1010-7, Jul. 2005.

Thomas Tischer, et al., "Detailed Pathological Changes of Human Lumbar Facet joints L1-L5 in Elderly Individuals", Eur Spine J (Mar. 2006);15(3):308-15, Epub July, vol. 15, 2005.

Nicola C. Gries, et al., "Early Histologic Changer in Lower Lumbar Discs and Facet joints and their Correlation", Eur Spine J (2000) 9:23-29 © Springer-Verlag 2000, Feb. 2000.

Anil Sethi, et al., "Transforaminal Lumbar Interbody Fusion Using Unilateral Pedicle Screws and a Translaminar Screw", Eur Spine J (2009) 18:430-434 DOI 10.1007/s00586-008-0825-4, Mar. 2009.

Sung-Min Kim, M.D., et al., "A Biomechanical Comparison of Supplementary Posterior Translaminar Facet and Transfacetopedicular Screw Fixation after Anterior Lumbar Interbody Fusiion", J Neurosurg (Spine 1) 1:101-107, Jul. 2004.

Jee-Soo Jang, M.D., et. al., "Clinical Analysis of Percutaneous Facet Screw Fixation after Anterior Lumbar Interbody Fusion", J Neurosurg: Spine 3:40-46, Jul. 2005.

Jee-Soo Jang, M.D., et. al., "Minimally Invasive Transforaminal Lumbar Interbody Fusion with Ipsilateral Pedicle Screw and Contralateral Facet Screw Fixation", J Neurosurg: Spine 3:218-223, Sep. 2005.

Natalie M. Best, et al., "Efficacy of Translaminar Facet Screw Fixation in Circumferential Interbody Fusions As Compared to Pedicle Screw Fixation", J Spinal Disord Tech, vol. 19, No. 2, Apr. 2006.

John W. Klekamp, et. al., "Cervical Transfacet Versus Lateral Mass Screws: A Biomechanical Comparison", Journal of Spinal Disorders, vol. 13, No. 6, pp. 515-518, 2000, Lippincott Williams & Wilkins, Inc., Philadelphia: Dec. 2000.

Harri Pihajamäki, et al., "Tissue Response to Polyglycolide, Polydioxanone, Polylevolactide, and Metallic Pins in Cancellous Bone: An Experimental Study on Rabbits", Journal of Orthopaedic Research, Aug. 2006.

Youn-Kwan Park, M.D., "Facet Fusion in the Lumbosacral Spine: A 2-year Follow-Up Study", vol. 51, No. 1, Jul. 2002.

Albert C. Schmidt, M.D., et al., "Lumbar Fusion Using Facet Inlay Grafts", Southern Medical Journal, vol. 68, No. 2., Feb. 1975.

Philipp Schleicher, M.D., et al., "Biomechanical Evaluation of Different Asymmetrical Posterior Stabilization Methods for Minimally Invasive Transforaminal Lumbar Interbody Fusion", J. Neurosurg: Spine, vol. 9, Oct. 2008.

Yasuaki Tokuhashi, M.D., et al., "C1-C2 Intra-articular Screw Fixation for Atlantoaxial Posterior Stabilization", Spine vol. 25, No. 3, pp. 337-241, Lippincott Williams & Wilkins, Inc., Feb. 1, 2000.

Lisa A. Ferrara, et al., "A Biomechanical Comparison of Facet Screw Fixation and Pedicle Screw Fixation", Spine vol. 28, No. 12, pp. 1226-1234, Lippincott Williams & Wilkins, Jun. 15, 2003.

Yukihiro Kai, M.D., et al., "Posterior Lumbar Interbody Fusion Using Local Facet Joint Autograft and Pedicle Screw Fixation", Spine vol. 29, No. 1, pp. 41-46, Lippincott Williams & Wilkins, Inc., Jan. 1, 2004.

Frank M. Phillips, M.D., "Effect of Supplemental Translaminar Facet Screw Fixation on the Stability of Stand-Alone Anterior Lumbar Interbody Fusion Cages Under Physiologic Compressive Preloads", Spine vol. 29, No. 16, pp. 1731-1736, Lippincott Williams & Wilkins, Inc., Aug. 2004.

Akira Igarashi, M.D., et al., "Inflammatory Cytokines Released from the Facet Joint Tissue in Degenerative Lumbar Spinal Disorders", Spine vol. 29, No. 19, pp. 2091-2095, Lippincott Williams & Wilkins, Inc., Oct. 1, 2004.

* cited by examiner

ARTICULATING FACET FUSION SCREW

FIELD OF THE INVENTION

The present invention relates to methods and devices for spinal stabilization and fusion, and particularly to stabilization and fusion of a facet joint.

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface and an inferior articular surface. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. In the lumbar spine, for example, one form of treatment to stabilize the spine and to relieve pain involves the fusion of the facet joint.

One known technique for stabilizing and treating the facet joint involves a trans-facet fusion in which pins, screws or bolts penetrate the lamina to fuse the joint. Such a technique has associated with it the risk of further injury to the patient as such translamina facet instrumentation can be difficult to place in such a way that it does not violate the spinal canal and/or contact the dura of the spinal cord or the nerve root ganglia. Further, trans-facet instrumentation has been known to create a rotational distortion, lateral offset, hyper-lordosis, and/or intervertebral foraminal stenosis at the level of instrumentation.

Examples of facet instrumentation currently used to stabilize the lumbar spine include trans-lamina facet screws ("TLFS") and trans-facet pedicle screws ("TFPS"). TLFS and TFPS implants provide reasonable mechanical stability, but, as noted above, they can be difficult to place, have long trajectories, and surgical access can be confounded by local anatomy. In some instances these implants can result in some degree of foraminal stenosis.

Accordingly, there is a need for instrumentation and techniques that facilitate the safe and effective stabilization of facet joints.

SUMMARY OF THE INVENTION

The devices and methods disclosed herein relate to stabilization and/or fusion of a facet joint via intra-facet placement of a screw or screw-like device including an additional stabilization feature. The intra-facet fixation and fusion screw can be adapted to include various configurations for the efficient and safe placement of the screw within the facet joint. In addition, the articulating feature of the screw takes advantage of additional anchoring available from the external features of the screw shaft. In general, the device functions as a sort of mechanical key that prevents sliding motion between the diarthroidal surfaces of the facet joint as external anchoring features of the device are placed so as to oppose the natural motion of the facet joint and provide stabilization. Additionally, the intra-facet screw can be formed of or include a fusion-promoting bioactive material thereby providing a single device and method capable of both fixation and fusion of the facet joint.

A spinal implant is provided having an elongate member with a longitudinal axis and threads extending over at least a portion of the outer surface thereof. The implant includes a stabilization feature associated with the elongate member that is selectively configurable between a delivery configuration and a deployed configuration in which the stabilization feature is oriented at an angle with respect to the longitudinal axis of the elongate member. The stabilization feature can be coupled to the elongate member by a joint, hinge, or pivot which is configured to allow the stabilization feature to move between the delivery configuration and the deployed configuration.

In one aspect, the implant can include a stabilization feature in the form of an articulating member pivotably connected to a proximal portion of the elongate member. The articulating member can include motion resisting plates which extend over at least a portion thereof and which are configured to provide frictional opposition to motion in the deployed configuration.

In another aspect, the implant can include a stabilization feature in the form of two distinct articulating members pivotably connected to a proximal portion of the elongate member and which are capable of rotating relative to one another in the deployed configuration.

In a further aspect, the implant can include a stabilization feature in the form of at least one prong that is substantially recessed within the elongate member in the delivery configuration. An actuator is effective to move the prong to the deployed configuration in which the prong extends from the elongate member at an angle relative to the longitudinal axis of the elongate member. A lumen is formed within the elongate member and configured to receive the actuator.

The implant can alternatively include a stabilization feature in the form of an expanding sleeve that is positioned over at least a portion of an outer surface of the elongate member. The sleeve can have proximal and distal ends and at least one hinged arm at a location between the distal and proximal ends. An actuation member, such as a nut which is threadably mated to the elongate member, can be mated to the implant proximal to the proximal end of the sleeve. Distal movement of the actuation member is effective to compress the sleeve and move the hinged arm to an expanded configuration. In the delivery configuration, the sleeve is not expanded and in the deployed configuration, the sleeve is expanded.

Additionally, at least a portion of the implant can include a fusion-promoting bioactive material. For example, the implant (or at least a portion of the thread) can be formed of the fusion promoting material, the implant can include a coating comprising the fusion promoting material, and/or the implant can have a "cage-like" configuration wherein the fusion-promoting bioactive material is housed within a non-fusion promoting material. For example, the fusion-promoting material can be cortical allograft bone or a bioceramic-loaded bioabsorbable material.

The invention also relates to methods for facet joint fixation and fusion. In one embodiment, the method can include surgically delivering at least one implant to a facet joint in an intra-facet orientation. The implant can have at least one selectively deployable stabilization feature formed therein such that deploying the stabilization feature allows it to extend from the implant and engage a bony surface of the facet joint to oppose the natural motion of the facet joint. In addition, delivering the implant can include inserting a threaded distal tip of the implant so that it assumes a non-linear trajectory and follows a curvilinear pathway to be embedded in the bony surface of the facet joint.

In one exemplary method, the stabilization feature can be deployed so that a proximal portion of the implant is re-oriented relative to an embedded tip. In another embodiment, deploying the stabilization feature includes splitting or bifurcating two distinct articulating portions of a proximal or distal portion of the implant and allowing them to rotate relative to one another. In yet another exemplary method, the stabilization feature can be deployed by protracting at least one prong recessed within a lumen formed in the implant so as to embed the prong in the bony surface of the facet joint. In protracting the prong, it can be moved distally through the lumen so that it follows a predefined pathway to protrude through an opening in the implant. In a further exemplary method, deploying the stabilization feature includes compressing an expandable sleeve, thereby causing a hinged arm of the sleeve to extend outwards from the implant to engage the bony surface of the facet joint. The stabilization feature can also be deployed such that inserting the implant in osteoporotic bone using a threaded fit can prevent retraction or pull-out of the implant.

These and other aspects of the presently disclosed embodiments will be described in detail below.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
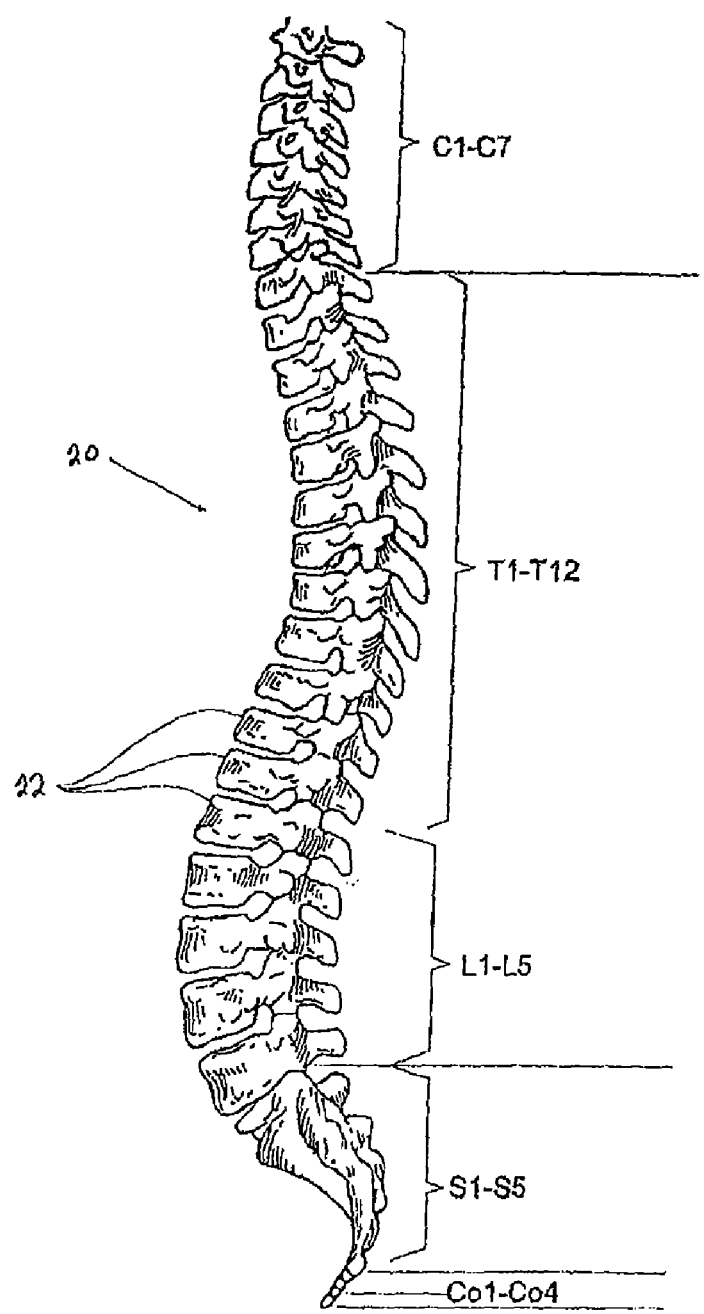
FIG. 1 is a representation of a human spinal column.
Figure 2:
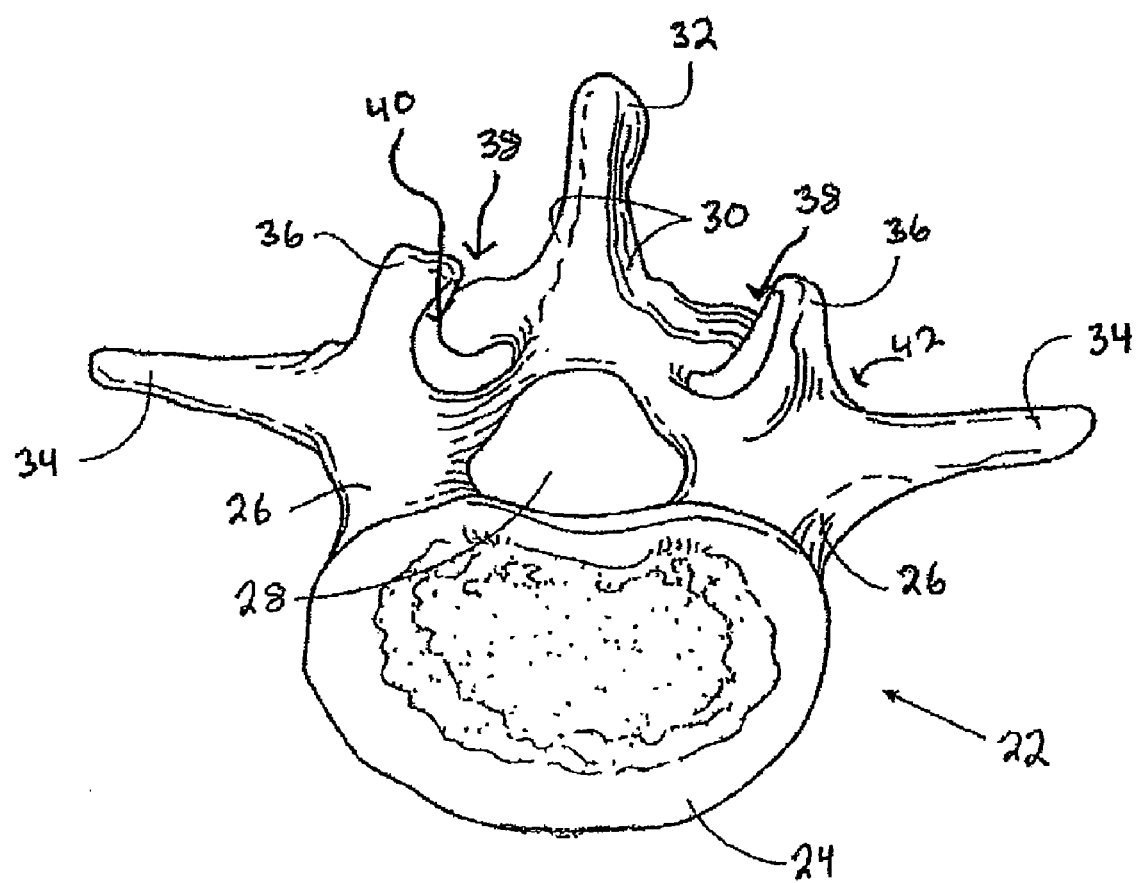
FIG. 2 is a representation of a lumbar vertebra.
Figure 3:
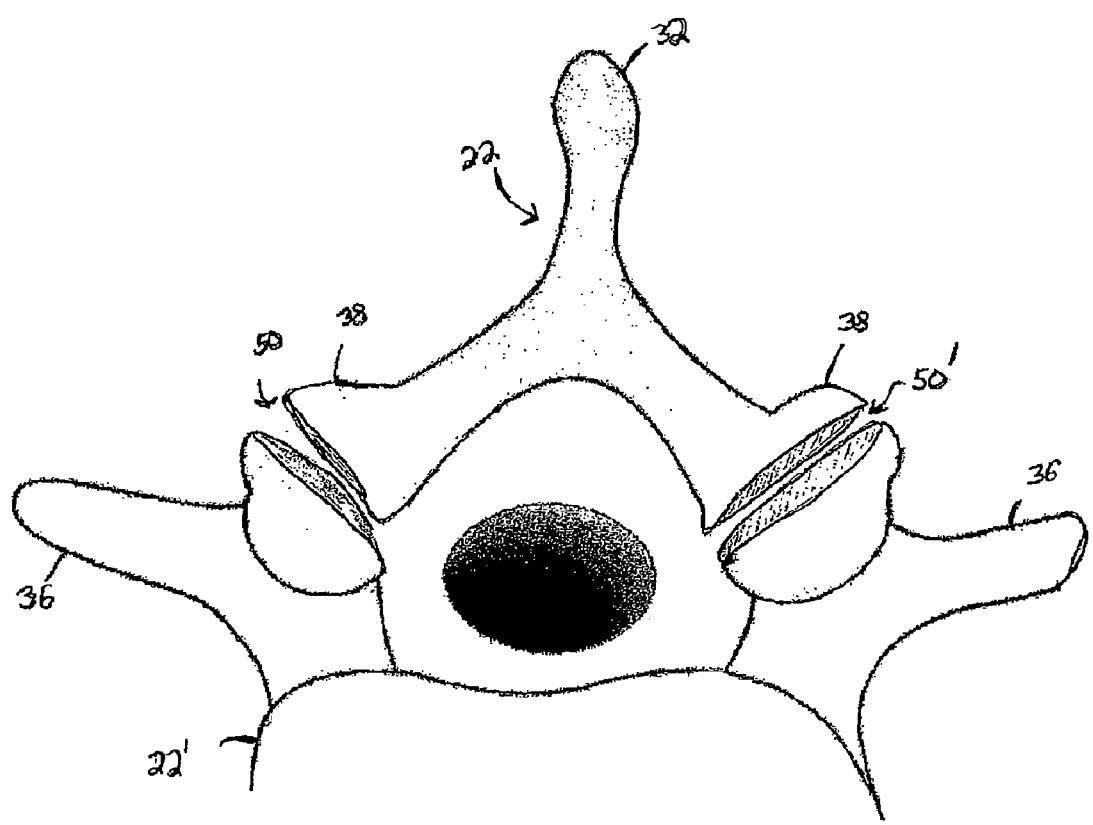
FIG. 3 is a representation of a first facet joint and a corresponding second facet joint formed as a result of a first vertebra stacked on a second vertebra.

FIGS. 1-3 provide an overview of the spinal column structure and location of associated facet joints. As FIG. 1 shows, the human spinal column 20 is comprised of a series of thirty-three stacked vertebrae 22 divided into five regions. The cervical region includes seven vertebrae 22, known as C1-C7. The thoracic region includes twelve vertebrae 22, known as T1-T12. The lumbar region contains five vertebrae 22, known as T1-T5. The sacral region is comprised of five vertebrae 22, known as S1-S5. The coccygeal region contains four vertebrae 22, known as Co1-Co4.

FIG. 2 shows a normal human lumbar vertebra 22. Although the lumbar vertebrae 22 vary somewhat according to location, they share many features common to most vertebrae 22. Each vertebra 22 includes a vertebral body 24. Two short bones, the pedicles 26, extend posteriorly from each side of the vertebral body 24 to form a vertebral arch 28. At the posterior end of each pedicle 26 the vertebral arch 28 flares out into broad plates of bone known as the laminae 30. The laminae 30 fuse with each other to form a spinous process 32, to which muscle and ligaments attach. A smooth transition from the pedicles 26 into the laminae 30 is interrupted by the formation of a series of processes.

Two transverse processes 34 thrust out laterally on each side from the junction of the pedicle 26 with the lamina 30. The transverse processes 34 serve as levers for the attachment of muscles to the vertebrae 22. Four articular processes, two superior 36 and two inferior 38, also rise from the junctions of the pedicles 26 and the laminae 30. The superior articular processes 36 are sharp oval plates of bone rising upward on each side from the union of the pedicle 26 with the lamina 30. The inferior processes 38 are oval plates of bone that jut downward on each side. The superior and inferior articular processes 36 and 38 each have a natural bony structure known as a facet. The superior articular facet 40 faces upward, while the inferior articular facet 42 faces downward. As shown in FIG. 3, when adjacent vertebrae 22, 22' are aligned (i.e., stacked), the facets interlock to form corresponding facet joints 50, 50' positioned at the same level of the spine.

Figure 4A:
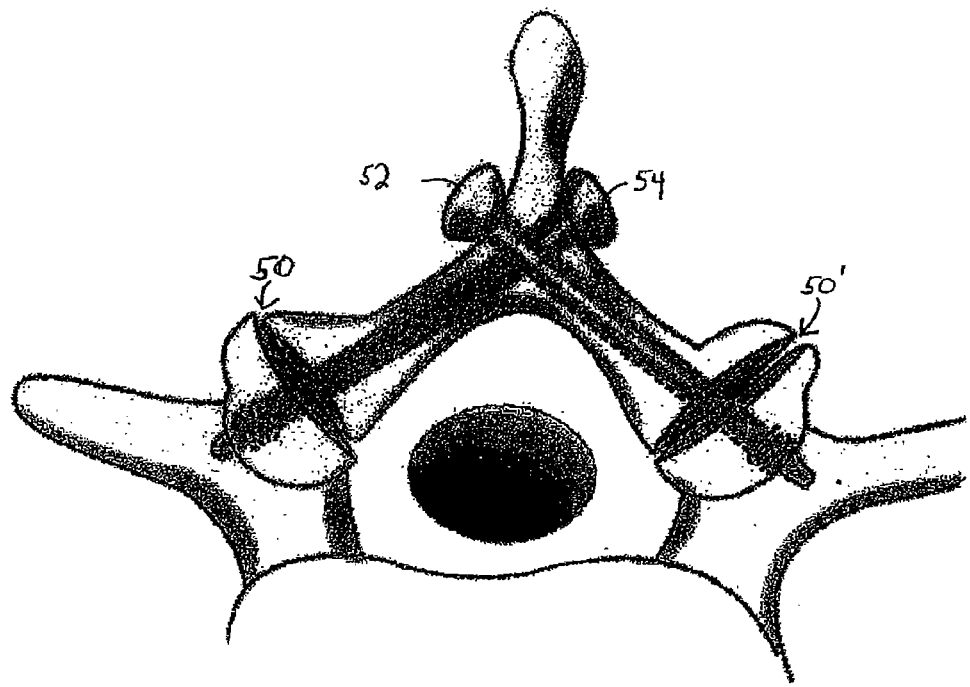
FIG. 4A is a representation of prior art trans-facet delivery of fixation screws.
Figure 4B:
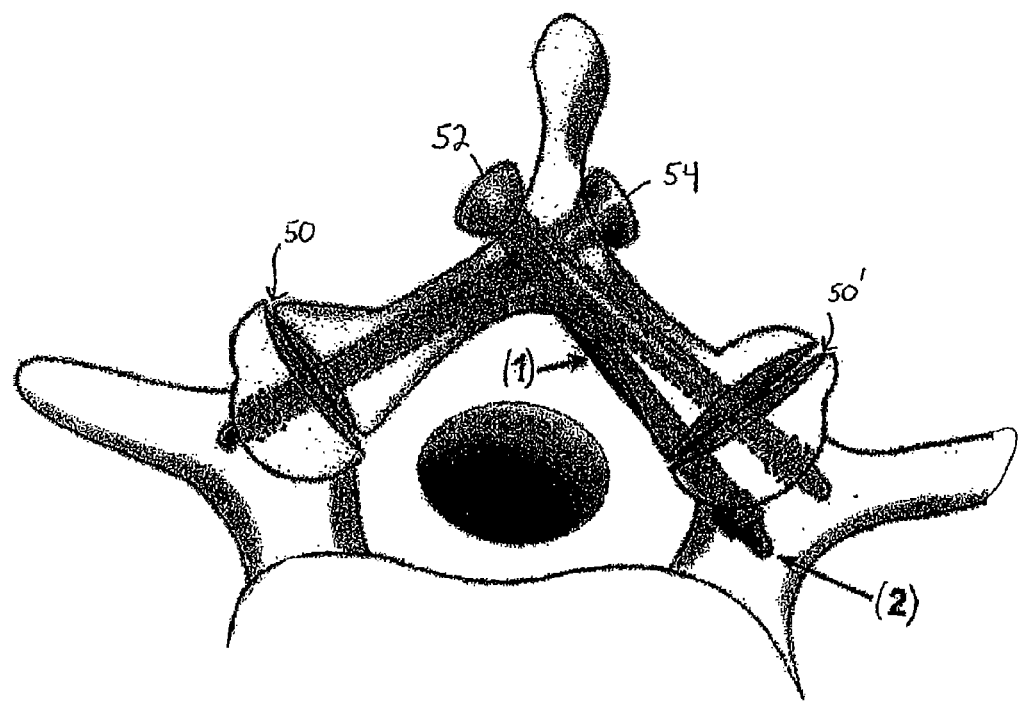
FIG. 4B is a representation of prior art trans-facet delivery of fixation screws wherein one of the trans-facet screws has impinged the spinal column.
Figure 4C:
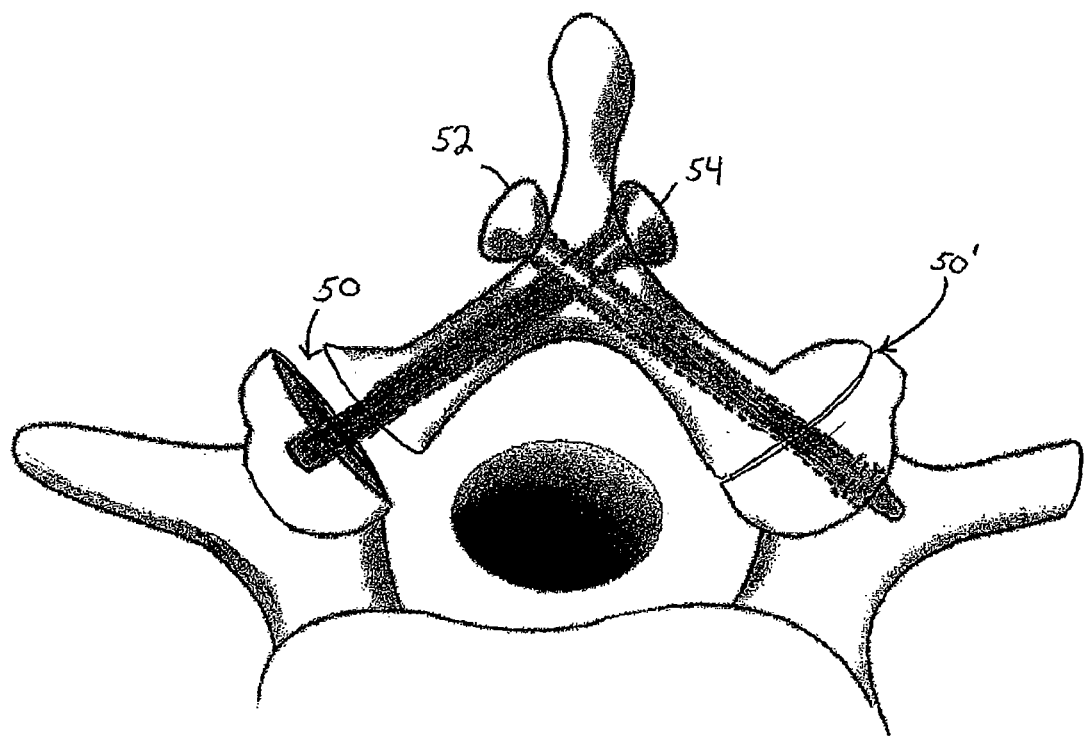
FIG. 4C is a representation of prior art trans-facet delivery of fixation screw wherein incorrect placement of the trans-laminar screws results in rotational distortion of the joint.

Looking in more detail at FIG. 3, the spinous process 32 and inferior articular processes 38 of the top vertebrae 22 are positioned adjacent to the superior articular processes 36 of the bottom vertebrae 22' and form facet joints 50, 50'. As shown in FIG. 4A, prior art trans-facet fixation procedure includes the insertion of trans-facet screws 52, 54 through bone and across the facet joints 50, 50'. However, such a procedure has been known to result in various problems. For example, FIG. 4B shows that a minor miscalculation in screw placement can result in a trans-facet screw 52 impinging upon the spinal column (as indicated by (1)) and/or surrounding nerves (as indicated by (2)), thereby resulting in patient injury. Additionally, trans-facet screw placement procedures can result in unwanted and/or unpredictable rotational distortion (or lateral offset) of the facet joint because of the difficulty of approximating the final position of the trans-facet screws 52, 54 in these procedures. As shown in FIG. 4C, trans-facet placement of the screws 52, 54 can result in significantly different gap sizes in corresponding facet joints 50, 50', thereby resulting in unwanted tension on the spine and ultimately injury to the patient.

Figure 5:
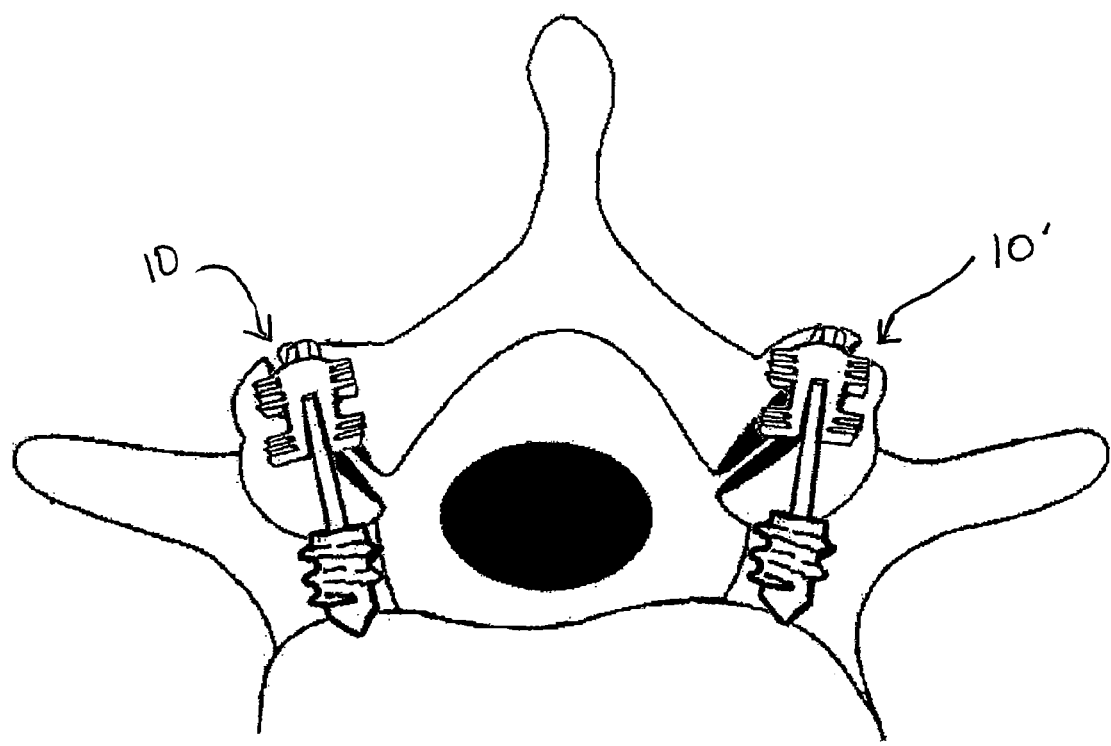
FIG. 5 is a representation of two presently disclosed articulating intra-facet screws placed within a facet joint.

In contrast to trans-facet screw placement techniques, the articulating facet fusion screws disclosed herein are configured to allow for intra-facet placement of the screw within the joint. FIG. 5 is an illustrative representation of articulating facet fusion screws 10, 10' positioned within corresponding facet joints 50, 50' at the same level of the spine in an intra-facet orientation. As shown, the intra-facet placement eliminates the need to pass the screw 10 through bone, but rather allows for delivery (in a minimally invasive manner, for example) along the plane (i.e., in an intra-facet orientation) of the facet joint 50, 50' such that the screw 10 engages and is positioned between the opposed superior and inferior faces of the facet joint. As represented in FIG. 5, an intra-facet screw 10 can be delivered bilaterally to both a first facet joint 50 and adjacent, second 50' facet joint at the same level of the spine.

In general, the presently disclosed embodiments relate to methods for intra-facet fixation and stabilization and to articulating and/or deformable intra-facet fusion screws or screw-like devices. The articulating fixation and fusion screws disclosed herein are configured for intra-facet delivery to the facet joint. That is, the screw is configured to be placed in the plane of the facet joint, between the diarthroidal surfaces of the facet joint. As such, the device functions as a sort of mechanical key that prevents sliding motion between the diarthroidal joint surfaces as external anchoring features of the device are placed so as to oppose the natural motion of the facet joint and provide stabilization. The intra-facet screw devices disclosed herein also stabilize the joint by distracting the facet faces and placing the joint capsule in tension. Such distraction of the facet face is believed to contribute to alleviating intervertebral foraminal stenosis. Further, intra-facet screws of the type disclosed herein include a selectively deployable articulating stabilization feature which allows the screw to take advantage of additional anchoring available from external features of the screw shaft.

The intra-facet screw can generally include an elongate member having a longitudinal axis and threads extending over at least a portion thereof. A common feature of the device is that the screw is articulatable and/or conformable between a delivery configuration and a deployed configuration. This can happen in many ways, but in general in the deployed configuration, the implant is able to serve the purpose of providing additional stabilization and resistance to motion in the facet joint via an articulating stabilization feature. The articulating stabilization feature is coupled to the elongate member via a joint, a pivot point, or any other coupling mechanism known in the art. The stabilization feature can be selectively configurable between a delivery configuration and a deployed configuration in which the stabilization feature is oriented at an angle with respect to the longitudinal axis of the elongate member. The screw can also accommodate a washer and nut assembly and at least a portion of the screw can include a fusion-promoting bioactive material formed thereon. In one embodiment, the screw can be cannulated, having an inner lumen extending through the screw, along the longitudinal axis thereof. These and other embodiments will be discussed below.

Figure 6A:
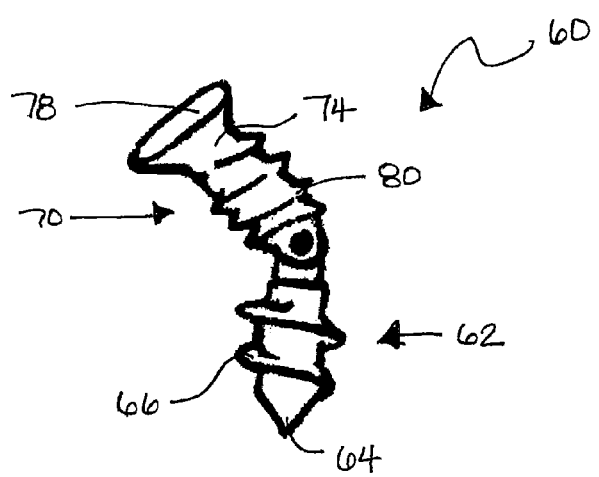
FIG. 6A is a front view of an embodiment of an articulating intra-facet screw in a deployed configuration.
Figure 6B:
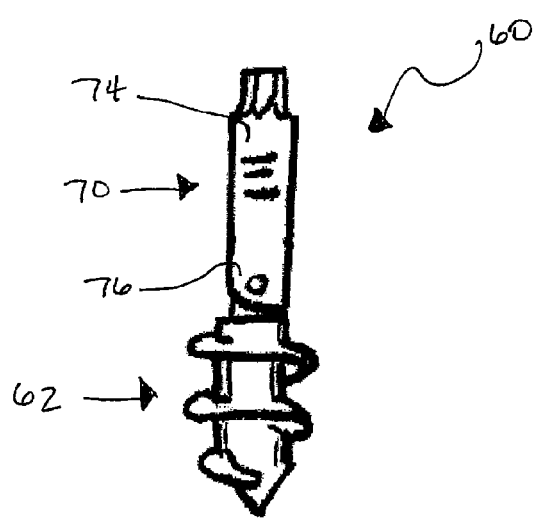
FIG. 6B is a front view of the articulating intra-facet screw of FIG. 6A in a delivery configuration.
Figure 6C:
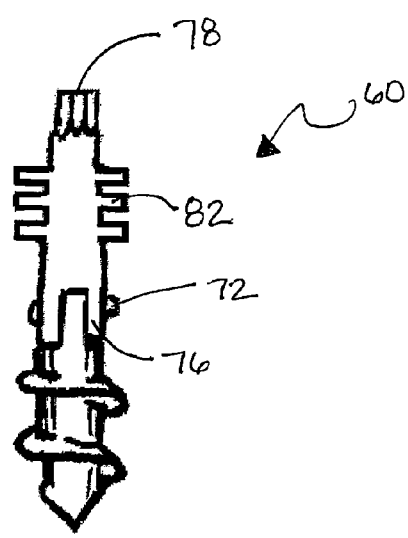
FIG. 6C is a side view of the articulating intra-facet screw of FIG. 6A in a delivery configuration.

FIGS. 6A-6C illustrate one embodiment of an intra-facet screw having an articulating stabilization feature configurable between a delivery configuration and a deployed configuration and providing additional anchoring for the screw within a facet joint. In the illustrated embodiment, an intra-facet screw 60 is provided having an elongate member 62 with a conical distal tip 64. The elongate member 62 can include threads 66, such as cantilever threads, extending around at least a portion thereof, allowing it to be rotationally inserted between the superior and inferior surfaces of the facet joint. As shown, a stabilization feature 70 is mated with the elongate member 62 by a hinge or pivot 72. A person skilled in the art will appreciate that a variety of other technologies can be used to mate the elongate member 62 and the stabilization feature 70. The hinge 72 can be located at any point along a length of the screw 60, and in the illustrated embodiment, the hinge 72 is located approximately midway along the length of the screw 60.

Figure 6D:
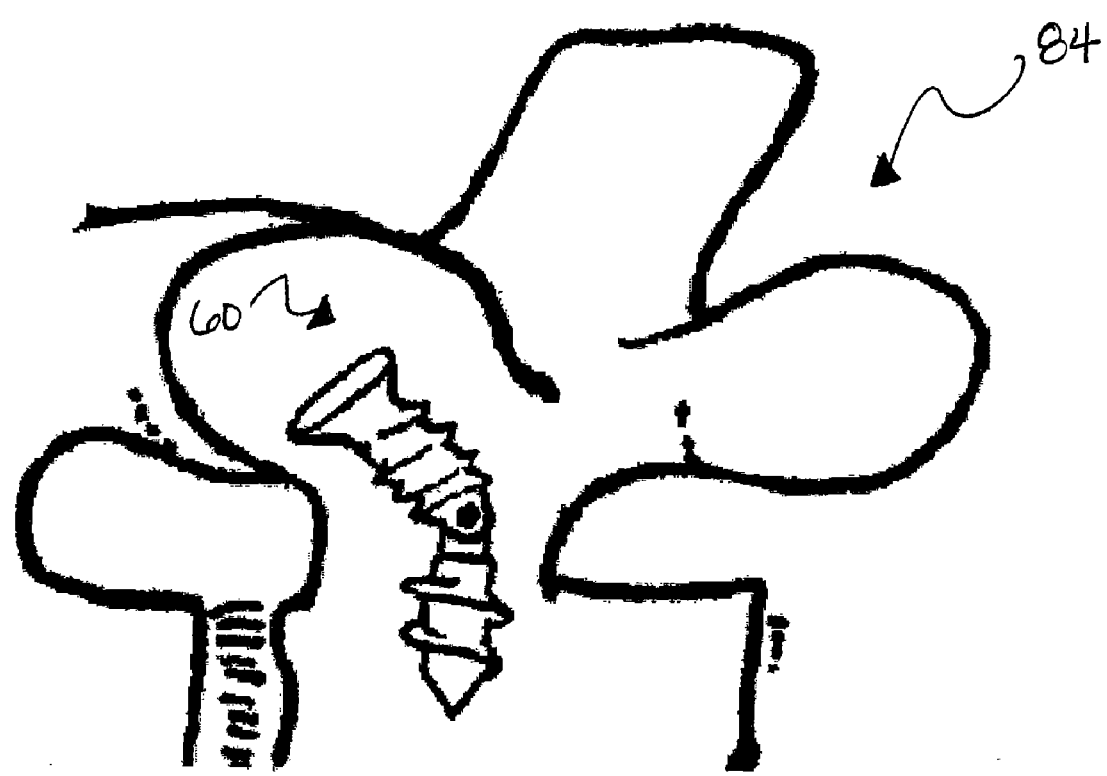
FIG. 6D is a representation of a deployed articulating intra-facet screw of FIG. 6A when placed within the facet joint to resist motion and provide stabilization.

The stabilization feature 70 can include an articulating member 74 having a distal end 76 coupled to the elongate member 62, as well as a proximal end 78 configured for receiving a drive tool. A person skilled in the art will appreciate that any drive tool which can be received by or applied to the screw 60 can be used. The articulating member 74 can have threads 80 extending around at least a portion thereof, as shown in FIG. 6A. Alternatively, motion resisting plates 82 can be formed along at least a portion of an exterior surface of the articulating member 74, as shown in FIG. 6C. The motion resisting plates 82 can be thin, rectangularly-shaped features which extend perpendicularly out from the articulating member 74. Both the cantilever threads 80 and the motion resisting plates 82 act to prevent the natural motion of the facet joint 84 when they are oriented in the direction of facet motion, as shown in FIG. 6D. The cantilever threads 80 and the motion resisting plates 82 are designed to embed in a bony surface of the facet joint 84, providing additional anchoring. A person skilled in the art will appreciate that any motion resisting surface, such as a knurled or grit blasted surface, can be formed along an exterior surface of the articulating member 74 to provide frictional opposition to the motion of the facet joint 84.

In use, the illustrated intra-facet screw 60 can initially be in a delivery configuration, as shown in FIGS. 6B and 6C. In such a configuration, the elongate member 62 and articulating member 74 are in line with one another during the delivery stage of a surgical procedure. A drive tool is applied to the proximal end 78 of the articulating member 74 and the screw 60 is rotationally inserted between the superior and inferior surfaces of the facet joint 84. As the screw 60 is inserted, the articulating member 74 can pivotably rotate relative to a longitudinal axis of the elongate member 62, allowing the screw 60 to follow a pathway or natural contour into the facet joint 84. Once positioned within the facet joint 84, the stabilization feature 70 can be deployed by re-orienting the articulating member 74 at an angle relative to the elongate member 62 which resists the natural motion of the facet joint 84. As shown in FIG. 6D, this allows the cantilever threads 80 or the motion resisting plates 82 to engage with and embed in the bony surface of the facet joint 84 and provide stabilization between the joints.

FIGS. 7A-7D illustrate another exemplary embodiment for an intra-facet screw having an articulating stabilization feature configurable between a delivery configuration and a deployed configuration and providing additional anchoring for the screw within a facet joint. In the illustrated embodiment, an intra-facet screw 100 is provided having an elongate member 102 with a conical distal tip 104. The elongate member 102 can include threads 106 extending over at least a portion thereof so that it can be rotationally inserted between the superior and inferior surfaces of the facet joint. As shown, a stabilization feature 110 is mated to the elongate member 102 by way of a hinge or pivot 112. A person skilled in the art will appreciate that a variety of other technologies can be used to mate the elongate member 102 and the stabilization feature 110. The hinge 112 can be located at any point along a length of the screw 100, and in the illustrated embodiment, the hinge 112 is located approximately midway along the length of the screw 100, which is also midway along a length of the stabilization feature 110 as well.

Figure 7A:
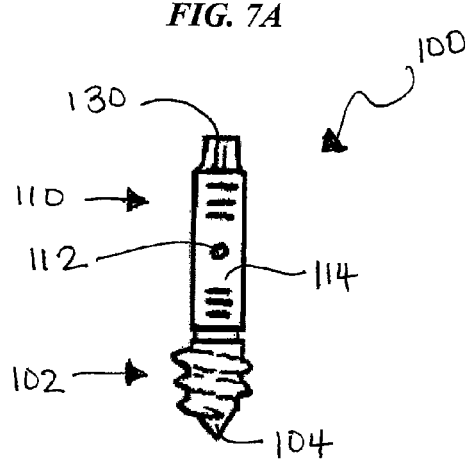
FIG. 7A is a front view of an embodiment of an articulating intra-facet screw in the delivery configuration wherein a top portion is solid.
Figure 7B:
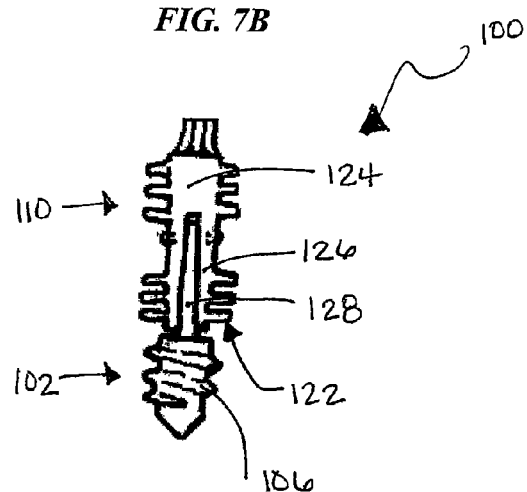
FIG. 7B is a side view of the articulating intra-facet screw of FIG. 7A.
Figure 7C:
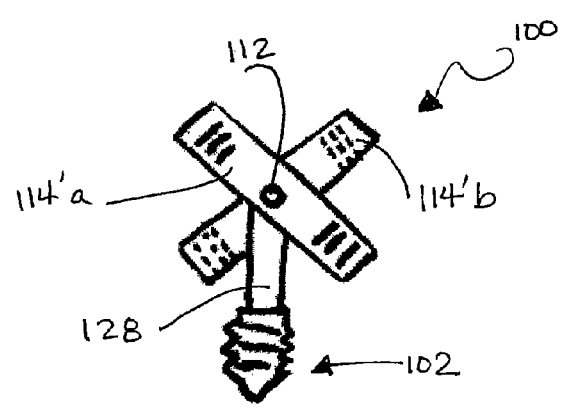
FIG. 7C is a front view of the articulating intra-facet screw of FIG. 7A in the deployed configuration wherein the top portion is bifurcated.
Figure 7D:
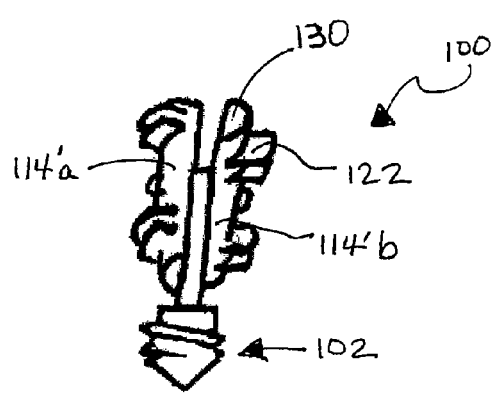
FIG. 7D is a side view of the articulating intra-facet screw of FIG. 7A in the deployed configuration wherein the top portion is bifurcated.

In the illustrated embodiment shown in FIGS. 7A and 7B, the stabilization feature 110 can include an articulating member 114 which can be divided into a solid proximal portion 124 and a bifurcated distal portion 126. The elongate member 102 can include a tongue 128 which extends proximally between the bifurcated distal portion 126 of the articulating member 114 to mate with the articulating member 114 at the hinge 112. Alternatively, as shown in FIGS. 7C and 7D, the stabilization feature 110 can include two distinct articulating members 114'a and 114'b which are mated to each other and to the elongate member 102 at the hinge 112. Articulating members 114 and 114'a, 114'b can include a proximal-most end 130 configured for receiving a drive tool. A person skilled in the art will appreciate that any drive tool which can be received by or applied to the screw can be used.

Figure 7E:
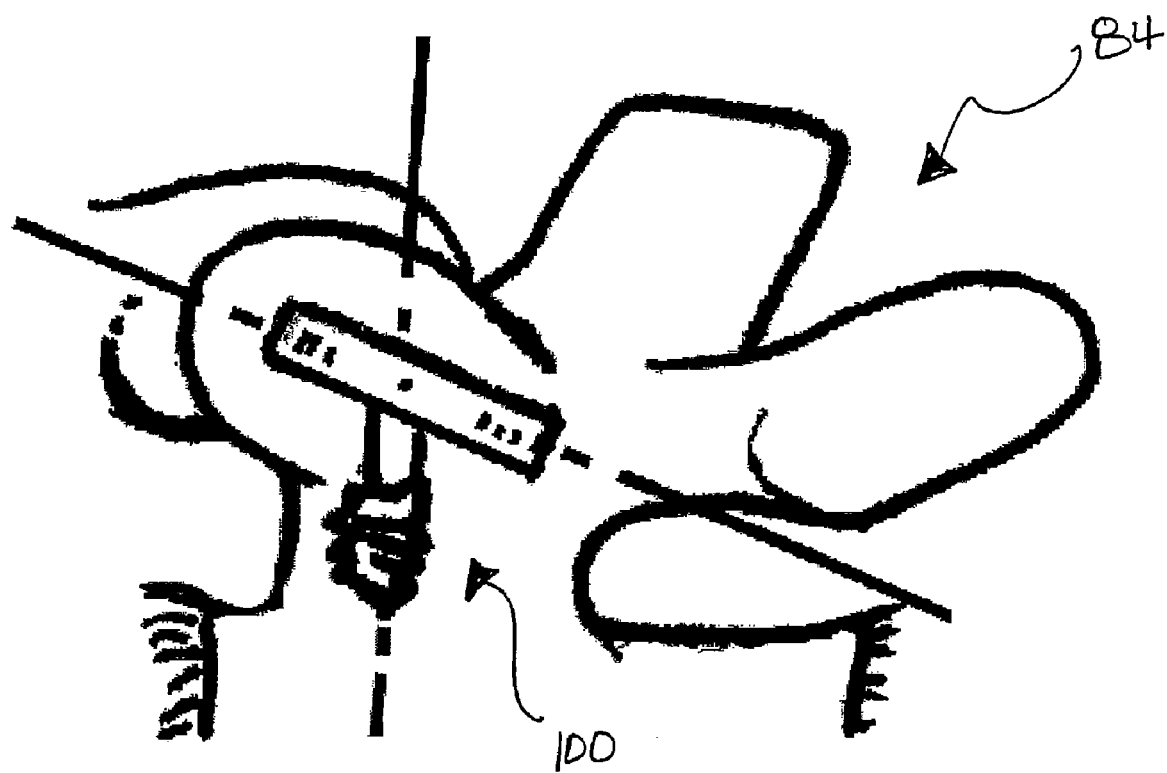
FIG. 7E is a representation of the articulating intra-facet screw of FIG. 7A when placed within the facet joint in the deployed configuration to resist motion and provide stabilization.

As shown in FIGS. 7A-7D, articulating members 114 and 114'a, 114'b can also have motion resisting plates 122 extending over at least a portion of an exterior surface thereof. The motion resisting plates 122 can be thin, rectangularly-shaped features which extend perpendicularly out from articulating members 114 and 114'a, 114'b. The motion resisting plates 122 act to prevent the natural motion of the facet joint 84 when they are oriented in the direction of facet motion, as shown in FIG. 7E. A person skilled in the art will appreciate that any motion resisting surface, such as a knurled or grit blasted surface, can be formed along an exterior surface of articulating members 114 and 114'a, 114'b to provide frictional opposition to the motion of the facet joint 84.

In use, the elongate member 102 and articulating members 114 and 114'a, 114'b can be initially in-line with each other for the delivery stage of a surgical procedure. A drive tool is used on the proximal-most end 130 of the stabilization feature 110 and the screw 100 is rotationally inserted between the superior and inferior surfaces of the facet joint. As the screw 100 is inserted, the hinge which connects the elongate member 102 and articulating members 114 and 114'a, 114'b allows the stabilization feature 110 to rotate relative to a longitudinal axis of the elongate member 102. In the embodiment shown in FIGS. 7C and 7D, the articulating member 114 can be rotated to any angle as needed with respect to the elongate member 102. In the embodiment shown in FIG. 7B, the two articulating members 114'a, 114'b can be bifurcated and rotated to any angle in different directions relative to each other to form the shape of an "X" as shown. In both embodiments, the rotation allows the screw 100 to follow a pathway or natural contour into the facet joint 84 as it is inserted. Once positioned within the facet joint 84, articulating members 114 and 114'a, 114'b can be pivotably rotated as needed so that the motion resisting plates 122 can engage with and embed in the bony surface of the facet joint 84 and provide stabilization and resist motion, as shown in FIG. 7E. A person skilled in the art will appreciate that the articulating members 114 and 114'a, 114'b can be rotated to any angle relative to the elongate member 102 as required by the procedure.

Figure 8A:
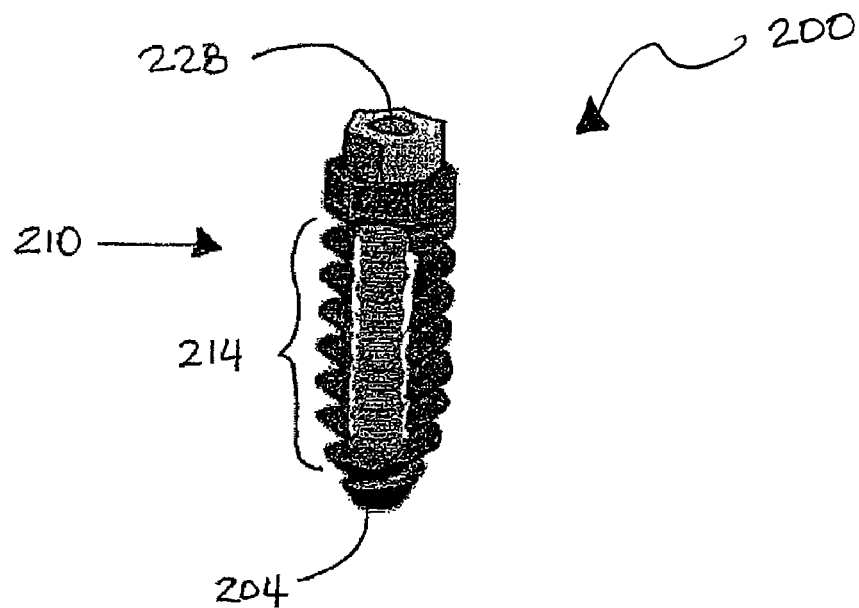
FIG. 8A is a perspective view of an embodiment of an articulating intra-facet screw in the delivery configuration.
Figure 8B:
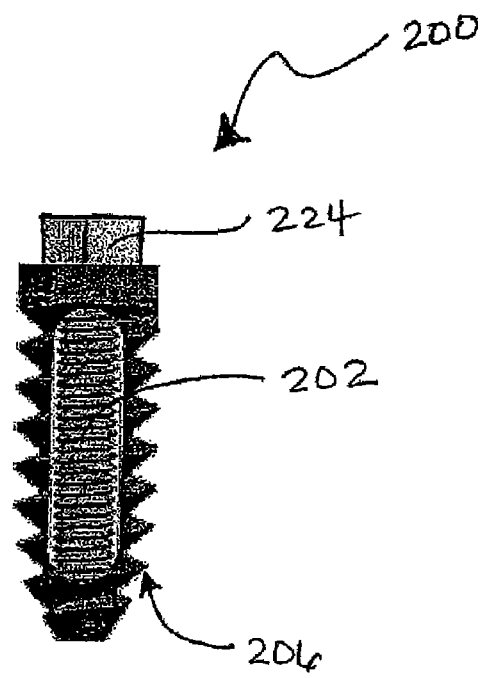
FIG. 8B is a front view the articulating intra-facet screw of FIG. 8A in the delivery configuration.

FIGS. 8A and 8B illustrate still another embodiment of an intra-facet screw having an articulating stabilization feature configurable between a delivery configuration and a deployed configuration and providing additional anchoring for the screw within a facet joint. In the illustrated embodiment, an intra-facet screw 200 is provided having a threaded elongate member 202 and a stabilization feature 210 which can include a conical distal tip 204 and threads 206 extending around at least a portion of an exterior surface thereof, allowing the screw 200 to be rotationally inserted between the superior and inferior surfaces of the facet joint. As shown, the stabilization feature 210 can include a compressible expansion sleeve 214 which encircles all or a portion of the elongate member 202. The sleeve 214 can have proximal and distal ends, and at least one hinged arm or a flexing point disposed at a location between the proximal and distal ends. In the illustrated embodiment shown in FIGS. 8A-8C, the sleeve 214 includes two hinged arms 226a, 226b extending between the proximal and distal ends of the sleeve 214 which allow the sleeve 214 to expand outward when compressed. A person skilled in the art will appreciate that a variety of other technologies can be used to allow the sleeve 214 to expand when compressed.

Figure 8C:
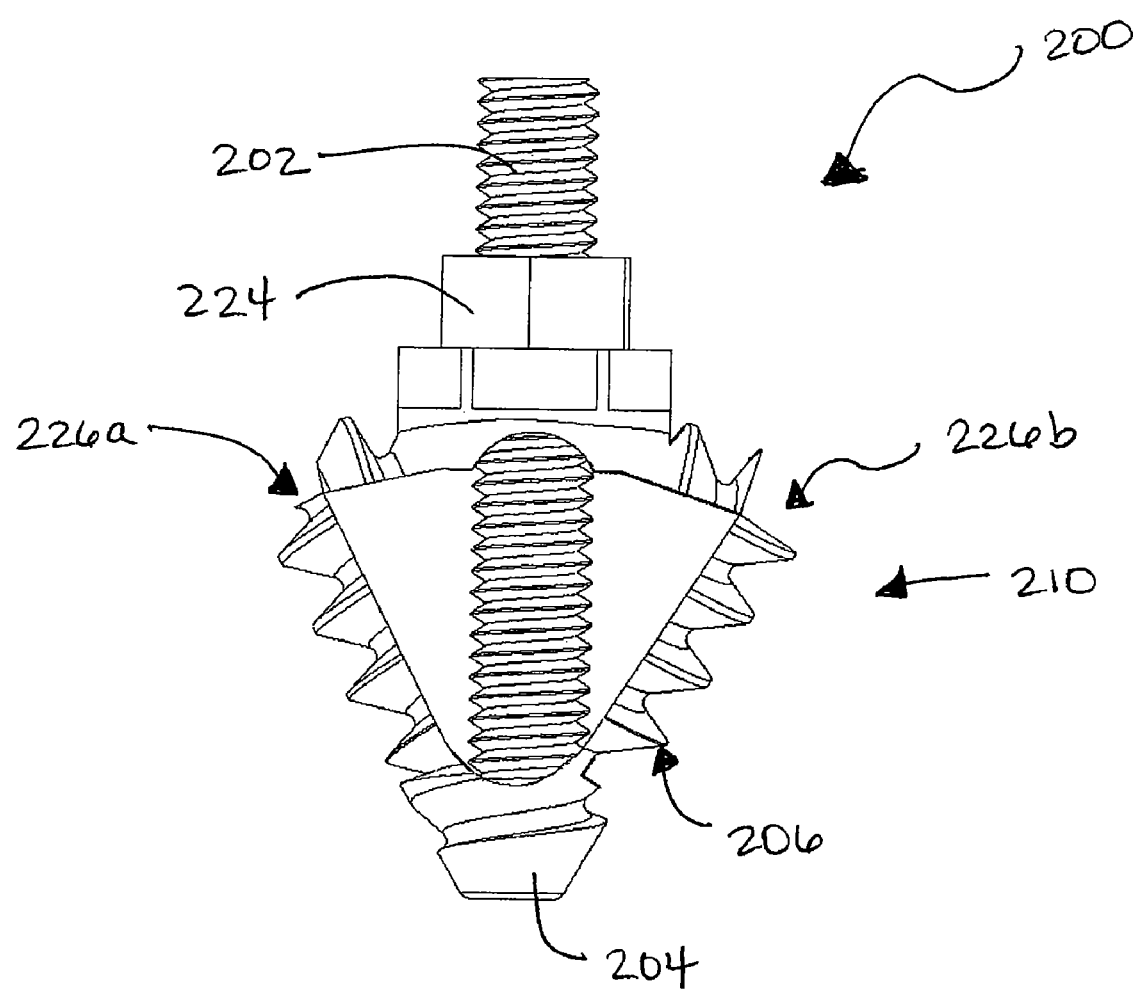
FIG. 8C is a front view of the articulating intra-facet screw of FIG. 8A in the deployed configuration.
Figure 8D:
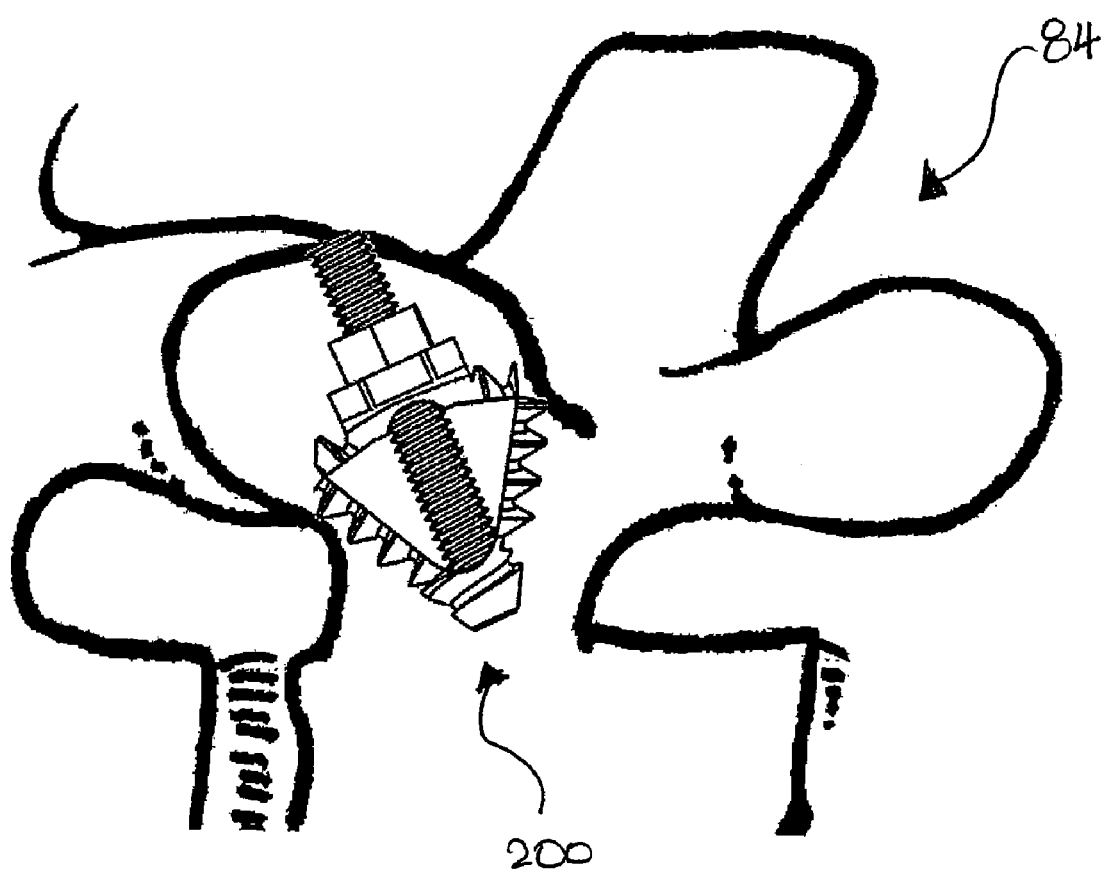
FIG. 8D is a representation of the articulating intra-facet screw of FIG. 8A when placed within the facet joint in the deployed configuration to resist motion and provide stabilization.

An actuation member can be mated to the screw 200 proximal to the proximal end of the sleeve 214 so that distal movement of the actuation member is effective to compress the sleeve 214 and cause it to expand outwardly. In the illustrated embodiment shown in FIGS. 8A-8C, the actuation member is a nut 224 which is threadably mated to the elongate member 202. In use, the nut 224 is initially at a proximal end 228 of the screw 200 as shown in FIG. 8A, and the sleeve 214 is uncompressed so that the sleeve 214 and the elongate member 202 are in-line with one another. A drive tool is applied to the proximal end 228 of the screw 200 and the screw 200 is rotationally inserted between the superior and inferior surfaces of the facet joint 84. Once the screw 200 is positioned within the facet joint 84, the nut 224 can be threaded distally along the threaded elongate member 202 (using the same or a different drive tool) thereby compressing the sleeve 214 and causing the hinged arms 226a, 226b to extend outward, as shown in FIGS. 8C and 8D. A person skilled in the art will appreciate that the nut 224 can be threaded distally to any place along the threaded elongate member 202 and that correspondingly, the sleeve 214 can be compressed and expanded to any position to provide anchoring as needed. The threads 206 located on the sleeve 214 can thus engage the bony surface as the hinged arms 226a, 226b are expanded outwards at an angle relative to the threaded elongate member 202, providing anchoring and resisting facet motion.

Figure 9A:
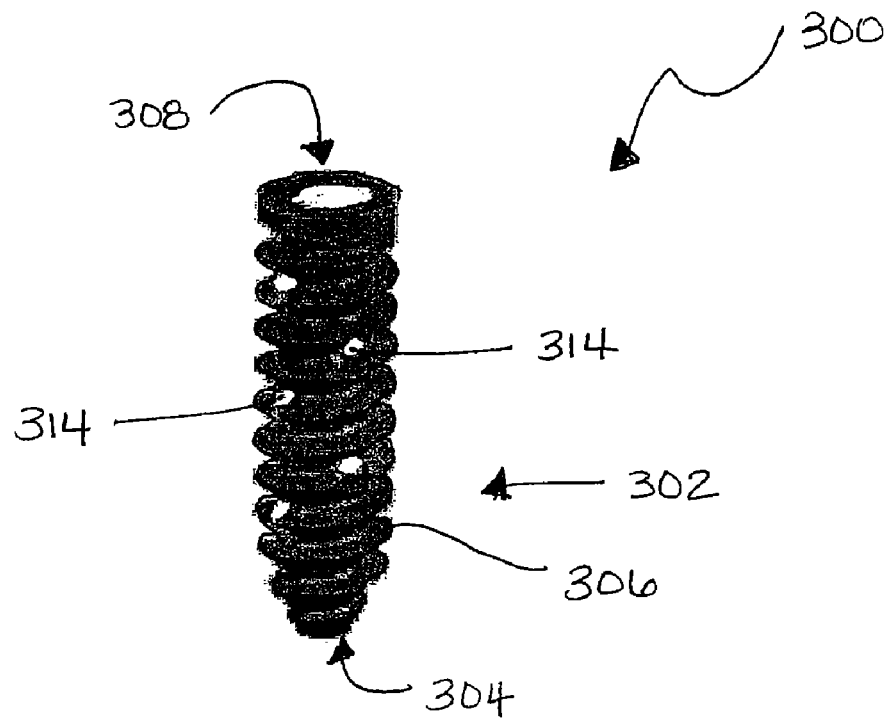
FIG. 9A is a perspective view of an embodiment of an articulating intra-facet screw in the delivery configuration.
Figure 9B:
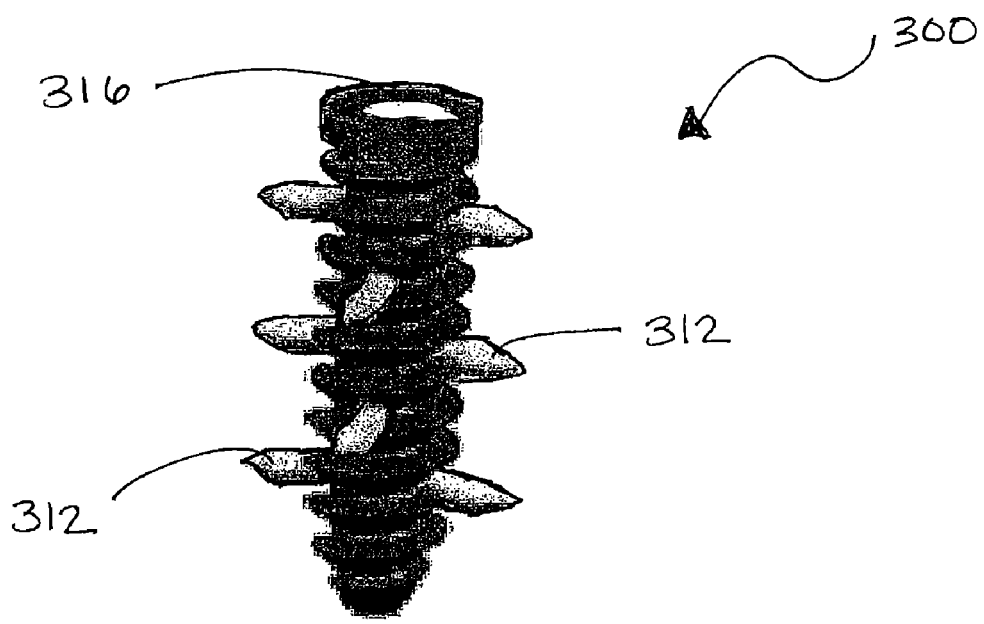
FIG. 9B is a perspective view of the articulating intra-facet screw of FIG. 9A in the deployed configuration.

FIGS. 9A and 9B illustrate a further embodiment for an intra-facet screw having an articulating stabilization feature configurable between a delivery configuration and a deployed configuration and providing additional anchoring for the screw within a facet joint. In the illustrated embodiment, an intra-facet screw 300 is provided having an elongate member 302 with a conical distal tip 304. The elongate member 302 can include threads 306 extending over at least a portion of an exterior surface thereof so that the screw 300 can be rotationally inserted between the superior and inferior surfaces of the facet joint. The elongate member 302 can include a lumen 308 formed therein and configured to house all or at least a part of a stabilization feature.

In the illustrated embodiment, the stabilization feature can include a spike-shaped prong system 312 which can be substantially recessed within the lumen 308 formed in the elongate member 302. Alternatively, at least a portion of the spike-shaped prongs 312 are recessed within lumen 308 and a portion of prongs 312 are recessed with respect to threads 306.

Figure 9C:
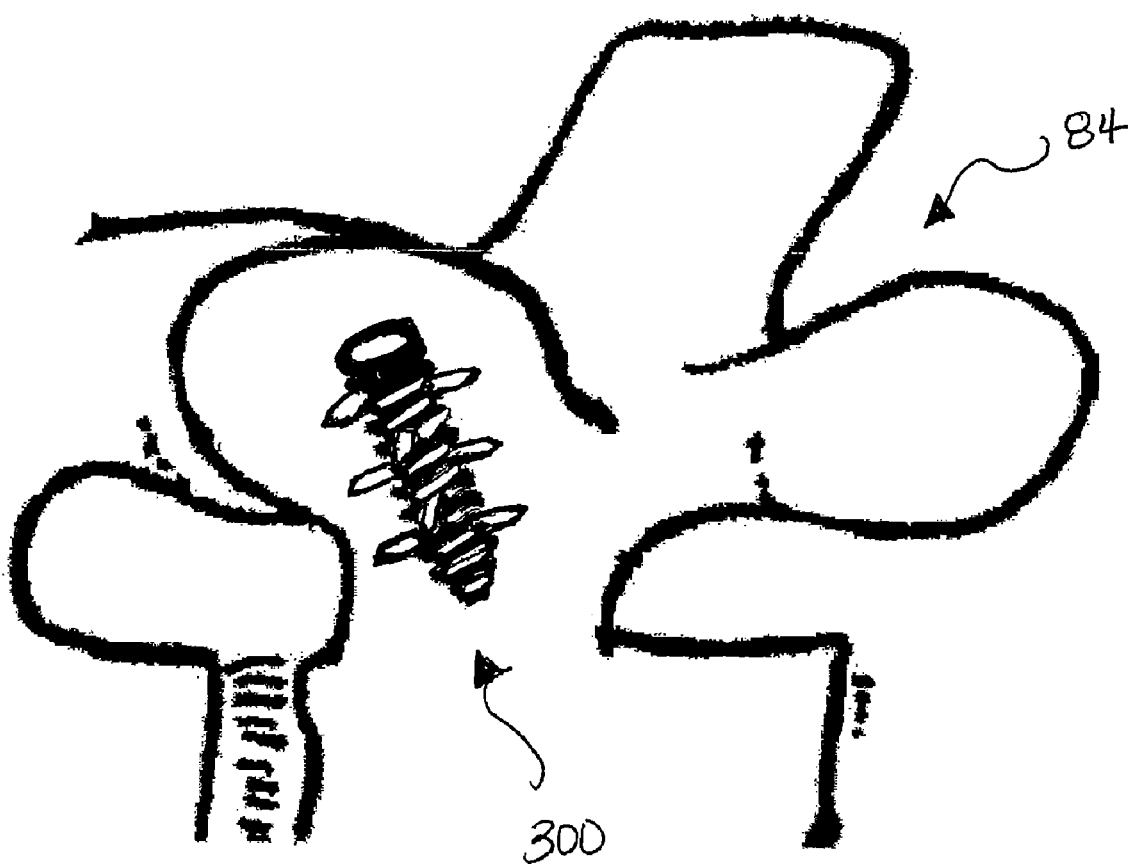
FIG. 9C is a representation of the articulating intra-facet screw of FIG. 9A when placed within the facet joint in the deployed configuration to resist motion and provide stabilization.

In use, a drive mechanism is applied to a proximal end 316 of the elongate member 302 and the screw 300 is rotationally inserted between the superior and inferior surfaces of the facet joint. During insertion, the screw 300 is in the delivery configuration so that the prongs 312 remain substantially recessed within the elongate member 302. Once positioned within the facet joint 84, a secondary drive mechanism (which can be the same as or different than a primary drive mechanism) can be applied to the lumen 308 to move the prongs 312 distally through the lumen 308 so that they follow a predefined path to protrude through corresponding openings 314 in the elongate member 302, as shown in FIGS. 9B and 9C. As the prongs 312 protrude from the elongate member 302, they can embed in the surface of the facet joint 84 to provide additional anchoring and prevent facet motion. A person skilled in the art will appreciate that any drive mechanism known in the art can be used to insert the screw 300 and deploy the prong system 312.

The methods and devices disclosed herein are also useful with poor quality bone, such as osteoporotic bone, as the threaded fit and stabilization features combine to prevent or resist retraction or pull-out of the device.

Intra-facet delivery provides physicians with a safe and efficient alternative to common trans-facet screw placement procedures. The selection of a suitable fixation device is simplified in that if an articulating intra-facet screw is not appropriately sized (e.g., too big, too small), it can be easily removed and replaced with an alternative device. Such a removal procedure can be effected by removing the screw from the plane of the facet joint as opposed to drilling a second passageway through bone (as would be required in trans-facet delivery). Further, intra-facet delivery requires less instrumentation (e.g., devices to drill bone) as compared to trans-facet stabilization procedures, thereby reducing the likelihood of contamination and/or infection resulting from the procedure. Furthermore, the simple nature of the intra-facet procedure results in significantly less trauma to the patient.

As an added benefit, the intra-facet screw and procedures disclosed herein are particularly well suited for minimally invasive surgery. That is, screws or similar devices can be placed in an intra-facet orientation using one or more small, percutaneous incisions, with or without the need for an access port. Such procedures, which are generally well known to those skilled in the art, tend to result in less operative trauma for the patient than a more invasive procedures. Minimally invasive procedures also tend to be less expensive, reduce hospitalization time, causes less pain and scarring, speed recovery, and reduce the incidence of post-surgical complications, such as adhesions.

In addition to the various features discussed above, the articulating intra-facet fusion screw can be adapted so as to allow for spinal fusion as well as spinal fixation. Any of the screw designs disclosed herein can include or be formed of a fusion-promoting bioactive material so that the screw actively participates in spinal fusion. In an exemplary embodiment, the screw is made from the bioactive material. In another embodiment, a bioactive material can be formed as a coating on a non-bioactive material from which the screw is formed. For example, the screw can be formed of a metal and be coated with a fusion-promoting bioactive material. Exemplary fusion promoting bioactive materials can include allograft bone, tricalcium phosphates (TCP), hydroxyapatite, Biocryl™ hydroxyapatite, bioglass, and polymer composites. Exemplary materials from which the screw can be formed include titanium, titanium alloys, ceramics, and polymers.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal implant, comprising:
   an elongate member extending along a longitudinal axis and having threads extending over at least a portion of the outer surface thereof; and
   a stabilization feature having threads extending over at least a portion of an outer surface thereof, the stabilization feature including an articulating member pivotably coupled to a proximal portion of the elongate member by a pivot that allows the stabilization feature to be selectively configurable between a delivery configuration and a deployed configuration in which the stabilization feature is oriented and fixed at an angle with respect to the longitudinal axis of the elongate member,
   wherein the articulating member includes motion resisting plates extending over at least a portion of an exterior surface thereof and configured to provide frictional opposition to motion in the deployed configuration.

2. The implant of claim 1, wherein the implant includes a fusion-promoting bioactive material.

3. The implant of claim 2, wherein the fusion-promoting bioactive material is selected from the group consisting of cortical allograft bone and bioceramic-loaded bioabsorbable material.

4. A method for facet joint fixation and fusion, comprising:
   surgically delivering at least one implant to a facet joint in an intrafacet orientation in which the implant is aligned along a central longitudinal axis, the implant having a distal portion with a conical distal tip and a proximal portion that includes at least one selectively deployable stabilization feature; and
   deploying the stabilization feature such that it extends from the implant to engage a bony surface of the facet joint to oppose the natural motion of the facet joint, a longitudinal axis of at least a portion of the proximal portion being disposed at an angle relative to the central longitudinal axis of the distal portion after deployment of the stabilization feature.

5. The method of claim 4, wherein delivering the implant includes inserting a threaded distal tip of the implant into the facet joint so that it assumes a non-linear trajectory and follows a curvilinear pathway to embed in the bony surface of the facet joint.

6. The method of claim 4, wherein deploying the stabilization feature includes re-orienting the proximal portion of the implant relative to the embedded tip.

7. The method of claim 4, wherein deploying the stabilization feature includes bifurcating two distinct articulating portions of the proximal or distal portion of the implant, allowing them to rotate relative to one another.

8. The method of claim 4, wherein deploying the stabilization feature includes protracting at least one prong recessed within the implant so as to embed the at least one prong in the bony surface of the facet joint.

9. The method of claim 8, wherein protracting the at least one prong includes moving the at least one prong distally through the lumen so that it follows a predefined pathway to protrude through an opening in the implant.

10. The method of claim 4, wherein deploying the stabilization feature includes compressing an expandable sleeve distally, thereby causing a hinged arm of the sleeve to extend outwards from the implant to engage the bony surface of the facet joint.

11. The method of claim 4, wherein the surgically delivering step is performed in a minimally invasive procedure.

12. The method of claim 4, wherein deploying the stabilization feature includes inserting the implant in osteoporotic bone using a threaded fit so as to prevent retraction or pull-out of the implant.

13. A spinal implant, comprising:
an elongate member extending along a longitudinal axis and having threads extending over at least a portion of the outer surface thereof; and
a stabilization feature having threads extending over at least a portion of an outer surface thereof, the stabilization feature coupled to the elongate member by a pivot that allows the stabilization feature to be selectively configurable between a delivery configuration and a deployed configuration in which the stabilization feature is oriented and fixed at an angle with respect to the longitudinal axis of the elongate member,
wherein the stabilization feature comprises at least one prong which is substantially recessed within the elongate member in the delivery configuration.

14. The implant of claim 13, further comprising an actuator effective to move the at least one prong to the deployed configuration in which the at least one prong extends from the elongate member at an angle relative to the longitudinal axis of the elongate member.

15. The implant of claim 14, wherein a lumen formed within the elongate member is configured to receive the actuator which is effective to move the at least one prong to the deployed configuration.

16. A spinal implant, comprising:
an elongate member extending along a longitudinal axis and having threads extending over at least a portion of the outer surface thereof; and
a stabilization feature having threads extending over at least a portion of an outer surface thereof, the stabilization feature coupled to the elongate member by a pivot that allows the stabilization feature to be selectively configurable between a delivery configuration and a deployed configuration in which the stabilization feature is oriented and fixed at an angle with respect to the longitudinal axis of the elongate member,
wherein the stabilization feature is an expanding sleeve that is positioned over at least a portion of an outer surface of the elongate member, the sleeve having proximal and distal ends, and at least one hinged arm located between the proximal and distal ends.

17. The implant of claim 16, wherein an actuation member is mated to the implant proximal to the proximal end of the sleeve, and distal movement of the actuation member is effective to compress the sleeve and move the hinged arm to an expanded configuration.

18. The implant of claim 17, wherein the sleeve is not expanded in the delivery configuration and is expanded in the deployed configuration.

19. The implant of claim 17, wherein the actuation member is a nut threadably mated to the elongate member.

20. A spinal implant, comprising:
an elongate member extending along a longitudinal axis and having threads extending over at least a portion of the outer surface thereof; and
a stabilization feature having threads extending over at least a portion of an outer surface thereof, the stabilization feature coupled to the elongate member by a pivot that allows the stabilization feature to be selectively configurable between a delivery configuration and a deployed configuration in which the stabilization feature is oriented and fixed at an angle with respect to the longitudinal axis of the elongate member,
wherein the stabilization feature comprises two distinct articulating members pivotably connected to a proximal portion of the elongate member and which are capable of rotating relative to one another in the deployed configuration.

* * * * *